United States Patent [19]

Hoki

[11] Patent Number: 5,150,423
[45] Date of Patent: Sep. 22, 1992

[54] METHOD OF AND DEVICE FOR INSPECTING PATTERN OF PRINTED CIRCUIT BOARD

[75] Inventor: Tetsuo Hoki, Kyoto, Japan
[73] Assignee: Dainippon Screen Mfg. Co. Ltd., Japan
[21] Appl. No.: 727,826
[22] Filed: Jul. 9, 1991

[30] Foreign Application Priority Data

Jul. 10, 1990 [JP] Japan .................................. 2-183257

[51] Int. Cl.$^5$ .............................................. G06K 9/00
[52] U.S. Cl. .......................................... 382/8; 382/55
[58] Field of Search ....................... 382/8, 55; 358/101, 358/106, 107; 356/237; 364/489-491, 474.16

[56] References Cited

U.S. PATENT DOCUMENTS 4,692,943 9/1987 Pietzsch et al. ......................... 382/55
4,980,923 12/1990 Kawamoto et al. .................. 382/55

Primary Examiner—Leo H. Boudreau
Attorney, Agent, or Firm—Ostrolenk, Faber, Gerb & Soffen

[57] ABSTRACT

An objective printed circuit board to be inspected has a printed conductive pattern (550) thereon. The image of the objective printed board is read with an image reader to obtain an image signal. Prior to the image reading of the objective printed board, a reference printed board of the same type as the objective printed board is prepared, and the image thereof is read with the image reader. An edge image of a conductive pattern on the reference printed board is extracted and enlarged to generate an enlarged edge image (SEI). In inspection of the objective printed board, only areas belonging to the enlarged edge image are actually inspected and other areas are not subjected to the inspection.

26 Claims, 20 Drawing Sheets

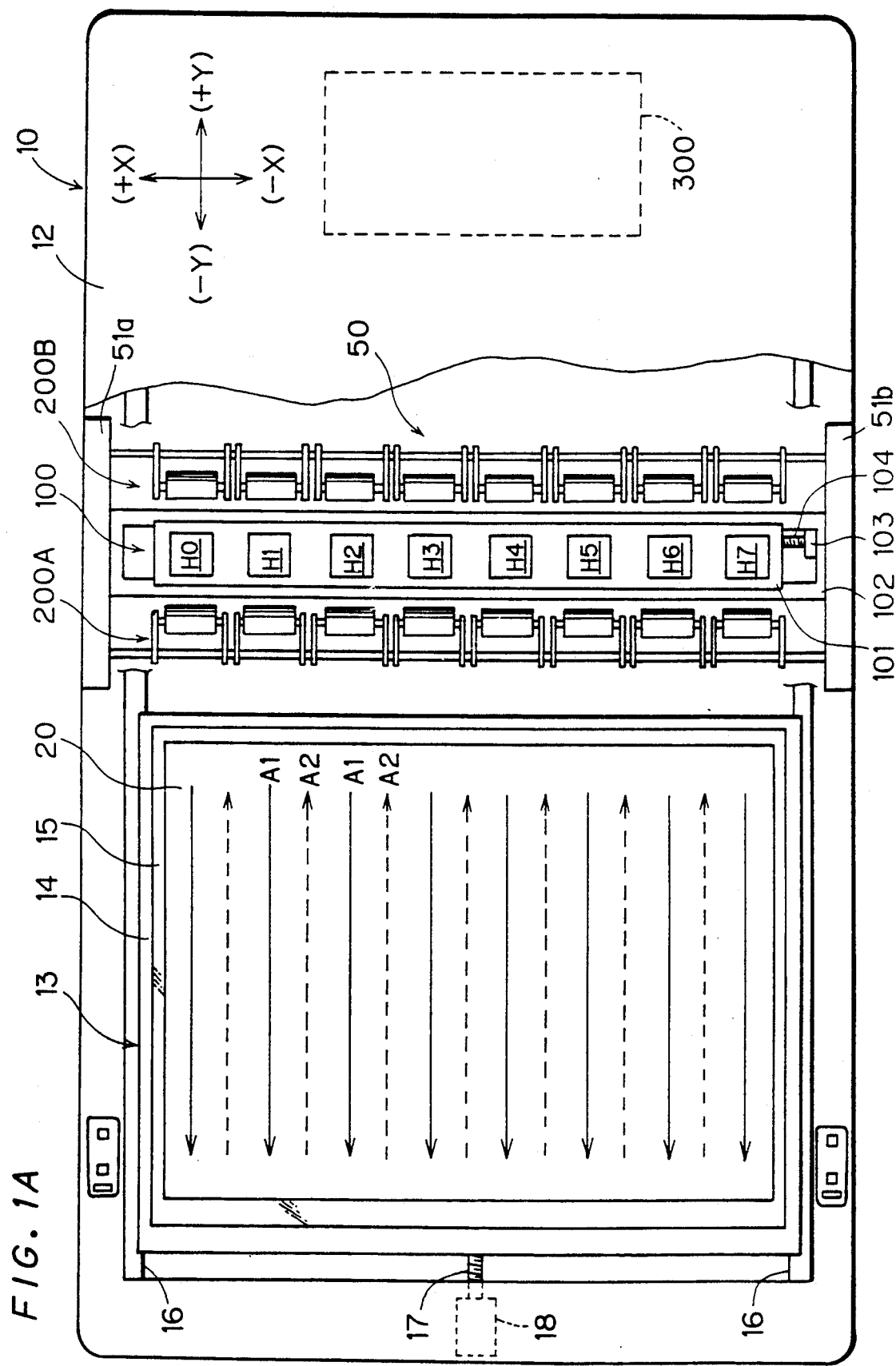

METHOD OF AND DEVICE FOR INSPECTING PATTERN OF PRINTED CIRCUIT BOARD

BACKGROUND OF THE INVENTION

1. Field of the Invention

The present invention relates to a method and a device for inspecting the pattern of a printed circuit board, and more particularly to a technique in which an inspection mode is selected depending on the location of pattern defects on the printed circuit board.

2. Description of the Background Art

Printed circuit boards are employed in the field of electronic engineering for mounting and interconnecting electronic elements. Such boards are provided with conductive wiring patterns on one or both sides of insulating boards and with a large number of through holes piercing the insulating boards. Various types of optical visual inspection devices or pattern inspection devices have been employed in order to inspect whether or not the conductive pattern and the through holes are formed accurately within a tolerance.

FIG. 16 is a partial plan view showing an exemplary conductive pattern which is provided on a printed board. The conductive pattern includes wiring patterns 901, lands 902, and shielding portions 903 for electrostatically shielding mounted electronic parts. Through holes (not shown) are formed in the respective lands 902. An optical pattern inspection device reads images of the conductive pattern and the through holes, and performs pattern inspection of the printed board on the basis of the images. The conductive pattern to be inspected may be a mixed pattern, which is provided with a source or grounding conductive pattern and a signal wiring pattern in a multilayer printed board, as well as an SMT (Surface Mount Technology) lead terminal pattern such as illustrated in FIG. 16.

A conventional pattern inspection device is structured so as to inspect the entire surface of a board according to a single inspection rule. Therefore, pinholes exceeding a prescribed size, for example, are judged as "defects" regardless of their location on the board surface.

However, even if the defects on the board are of the same type, their, degree of importance in quality control varies depending on the location of the defects thereof. For example, even a fine defect is liable to become a critical defect in the wiring area 910 of FIG. 16, while such a fine defect does not significantly influence the quality of the printed board in the central area 911 of the shielding portion 903. Thus, printed boards which are judged as defective by a conventional pattern inspection device include those boards that are usable; i.e., nondefectives. For example those having a fine defect only in the aforementioned central area 911. Therefore, a complicated operation is required in order to confirm whether printed boards being judged as defective are actually non-usable defectives or are printed boards which may be considered nondefective. Such and operation leads to a low output of the entire inspection process.

SUMMARY OF THE INVENTION

The present invention is directed to a method of inspecting an objective printed board having a conductive pattern thereon.

According to the present invention, the method comprises the steps of: (a) obtaining an image of the objective printed board, wherein the image includes an image of the conductive pattern; (b) extracting an edge of the conductive pattern from its image, or from an image substantially equivalent to the image of the conductive pattern, to generate an edge image; (c) enlarging the width of respective portions of the edge image to generate an enlarged edge image; (d) determining first and second areas in the image of the objective printed board, wherein the first area coincides with the aforementioned enlarged edge image and the second area is an area other than the first area; and (e) inspecting the first area of the image of an objective printed board in a first inspection mode and inspecting the second area of the image of the objective printed board in a second inspection mode different from the first inspection mode.

In one aspect of the present invention, a reference printed board is prepared tat is identical to an objective printed board having a conductive pattern previously judged as nondefective. The image of the reference printed board is read, prior to the image reading of the objective printed board, to obtain the edge image described in the step (b) above.

In a preferred embodiment of the present invention, only the first area is actually inspected and the second area is not subjected to inspection.

Alternatively, an image of a mask film used in forming the objective printed board may be utilized, or design data of the printed board may be utilized for performing the aforementioned edge extraction.

The term "the image substantially equivalent to the image of the conductive pattern" in the present invention is generic and encompasses the aforementioned images or image data.

Preferably, regions where mini via holes exist are removed from the enlarged edge image.

The present invention also provide a device suitable for operation based on the present method.

The selection or switching of inspection modes in the present invention includes the following cases:

(1) ON-OFF Switching

. An inspection is actually performed in an ON-mode, while no inspection is performed in an OFF mode.

(2) Inspection Condition Switching

The degree of strictness in inspection is changed depending on whether the objective area inspected belongs to the enlarged edge image. Thus, for example, the Inspection Condition Switching includes the switching of the maximum allowable diameters of pinholes in two ways, for example.

(3) Inspected Item Switching

Inspected items are switched depending on whether the objective area inspected belongs to the enlarged edge image. For example, the Inspected Item Switching includes switching between performing hole breakout inspection in the enlarged edge images area and performing inspection of pinholes in non-edge regions.

The present invention is based on the fact that defects caused in areas around edges of a conductive pattern are important in quality control. In addition to wiring patterns, defects such as around the edges of shielding portions are liable to relate to other defects in later stages of board fabrication. This may result in a reduction in reliability of the printed circuit board. According to the present invention, such areas are grasped as "enlarged edge images" by combination of edge extraction means and edge enlarging means. In an image of the printed board, different inspection modes are selectively employed in enlarged edge regions defined by the enlarged edge images as compared to other non-edge regions, thereby enabling suitable pattern inspection in consideration of portions that are likely to cause defects.

Accordingly, an object of the present invention is is to provide a pattern inspection method and device for a printed board which can detect pattern defects while distinguishing areas having a high degree of importance in quality control from other areas having a lesser degree of importance. As a result, the entire inspection process is improved by omitting or simplifying the confirming operation which customarily follows the detection of pattern defects in printed circuit boards.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 1A is a partially fragmented plan view showing an optical inspection device for a printed board according to a preferred embodiment of the present invention.

DESCRIPTION OF THE PREFERRED EMBODIMENTS

A. Structure

Figure 1B:
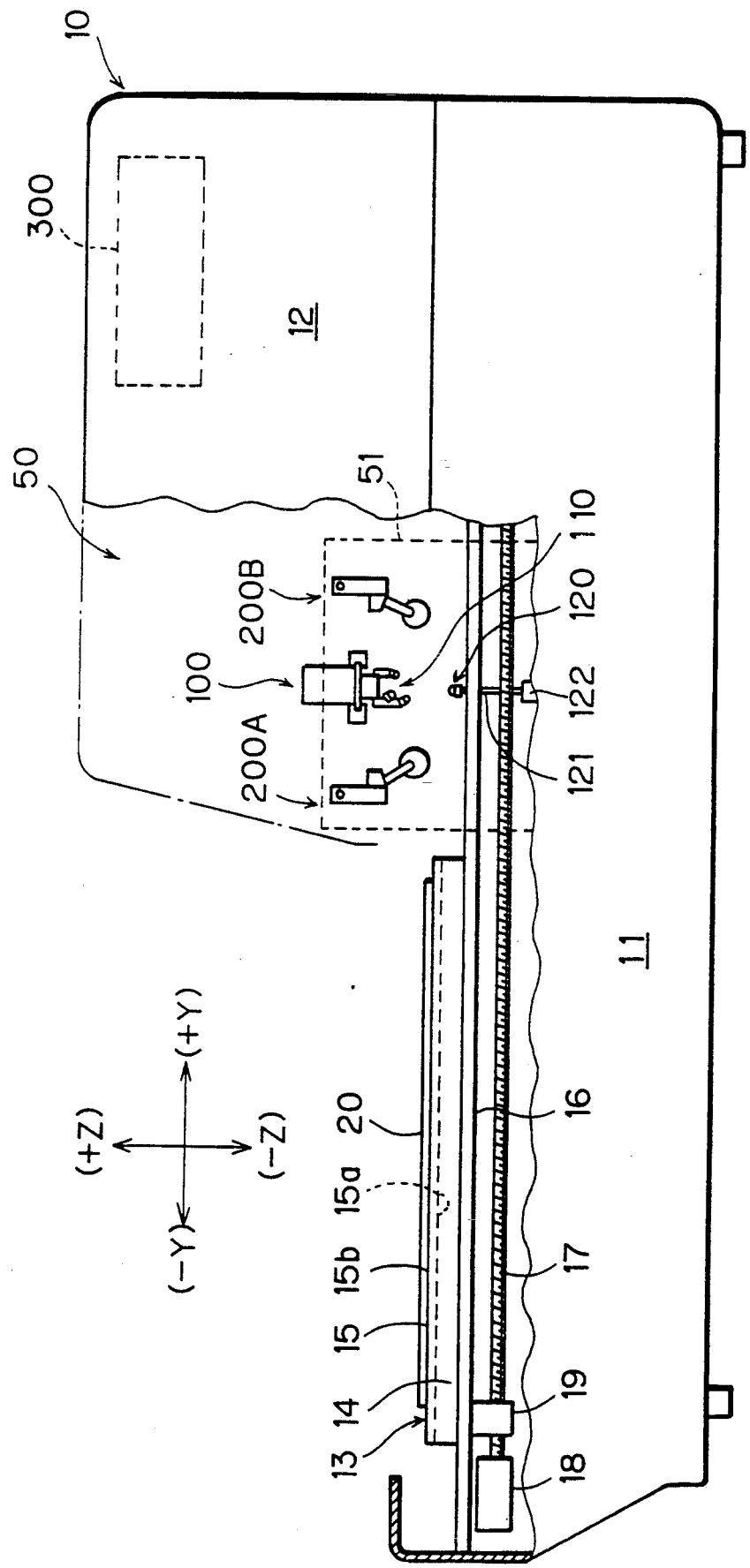
FIG. 1B is a partially fragmented side elevational view of the device shown in FIG. 1A.

FIG. 1A is a plan view, with portions broken away, of a printed circuit board inspection device 10 according to a preferred embodiment of the present invention, and FIG. 1B is a side view thereof. The device 10 comprises a lower housing 11 and an upper housing 12. The lower housing 11 is provided with a horizontally movable table 13. The movable table 13 includes a rectangular frame 14 and a glass plate 15 mounted in the rectangular frame 14. The bottom surface 15a of the glass plate 15 is frosted or coarsely ground. A printed circuit board 20 is placed on the top surface 15b of the glass plate 15 and is supported by the glass plate 15.

Figure 2:
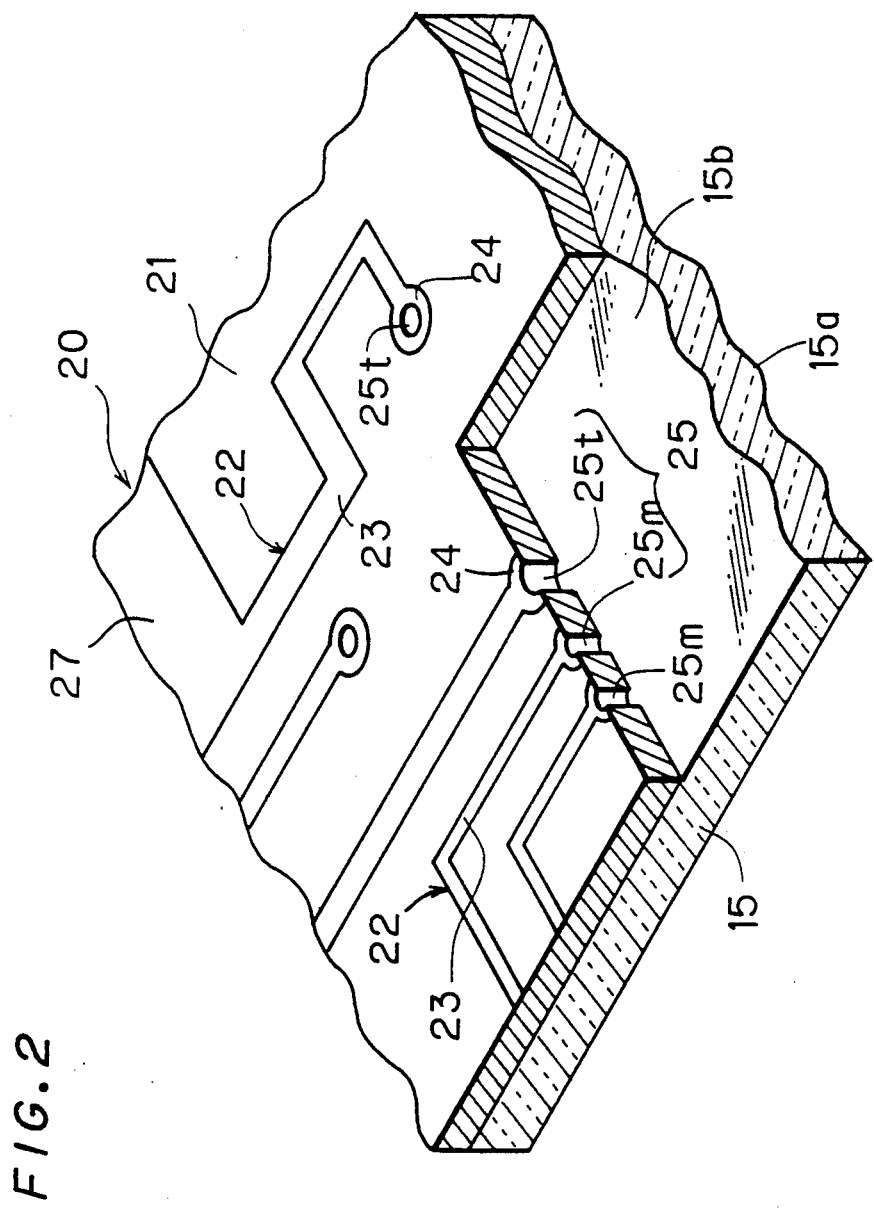
FIG. 2 illustrates an exemplary printed board.

With reference to FIG. 2, the printed circuit board 20 includes an insulative base plate 21 made of glass epoxy and printed patterns or conductive patterns 22 of copper formed on both surfaces thereof by means of screen printing technique or photo-etching technique. The printed patterns 22 have wiring pattern portions 23, lands 24, and a shield portion 27. Each of the lands 24 is formed therein with a through-hole 25 which pierces or penetrates through the printed circuit board 20. The through-holes 25 are classified into two types: normal through-holes 25t and mini via-holes 25m. The normal through-holes 25t, having a relatively large diameter, are used for mounting electronic elements and for connecting the electronic elements to the conductive patterns 22. The mini-via-holes 25m, having a relatively small diameter, are used for electrical connection between the two surfaces of the insulative base plate 21. The inner wall surfaces of the through-holes 25t and 25m are plated with conductive metal.

Reference is made to FIGS. 1A and 1B. The frame 14 is slidable on a pair of guide rails 16. A ball screw 17 extends in the direction parallel to the guide rails 16. A nut 19, fixed to the frame 14, is coupled with the ball screw 17. When a motor 18 turns the ball screw 17, the movable table 13 moves in the horizontal ($\pm Y$) directions.

An image reading system 50 is provided in the upper housing 12. An optical head array 100 extending in the horizontal ($\pm X$) directions is disposed in a space over the mid portion of the image reading system 50. The optical head array 100 includes eight optical heads H0 to H7, which are supported at equal intervals by a supporting member 101. The supporting member 101 is slidable on a guide member 102 in the ($\pm X$) directions. The guide member 102 is fixed to a pair of side frame members 51a and 51b. The supporting member 101 is coupled to a motor 103 through a nut (not shown) and a ball screw 104. When the motor 103 is driven, the optical heads H0 to H7 move in the ($\pm X$) directions together with the supporting member 101.

A light source 120 for "transmitted illumination" is disposed under the optical heads H0 to H7. As used herein, "transmitted illumination" is defined as illumination applied to an object and transmitted through holes formed in the object. The light source 120 is composed of a large number of infrared LEDs arranged in the ($\pm X$) directions, and serves substantially as a linear light source. The light source 120 is supported from the side frames 51 through supporting rods 121 and 122. Each of the optical heads H0 to H7 has a light source 110 for "reflected illumination". The light source 110 being attached to the bottom thereof. "Reflected illumination" is defined as illumination applied to an object and reflected at the surface of the object. The light source 110 includes three pairs of one-dimensional arrays of red LEDs extending in the ($\pm X$) directions.

Presser roller mechanisms 200A and 200B are provided on opposite sides of the optical head array 100 in order to press the printed circuit board 20 fed thereunder. The presser roller mechanisms 200A and 200B operate to prevent the out-of-position and flexure of the printed circuit board 20.

A data processor 300 for performing various data processings and operation controls is disposed in the upper housing 12.

B. Overall Operation

Prior to the description of the detailed structure of the inspection device the overall operation of the device 10 will be discussed hereinafter. Initially, the printed circuit board 20 is placed on the glass plate 15 as shown in FIGS. 1A and 1B. When an operation switch is manually operated, the motor 18 is rotated forward so that the printed circuit board 20 moves in the (+Y) direction together with the movable table 13. The light sources 110 and 120 light up.

Next, the printed circuit board 20 reaches the position of the image reading system 50 with the movement of the table 13. The optical heads H0 to H7 read the images of the printed patterns 22 (of FIG. 2) illuminated by the reflected illumination from the light source 110, and read the images of the through-holes 25 illuminated by the transmitted illumination from the light source 120. The respective image reading is conducted for each scanning line schematically defined on the printed circuit board 20.

Since there are gaps between the visual fields of the respective optical heads H0 to H7, the entire image of the surface of the printed circuit board 20 cannot be read only through a movement of the printed circuit board 20 in the (+Y) direction. Therefore, after the movement of the printed circuit board 20 in the (+Y) direction, the motor 103 is driven to move the optical heads H0 to H7 in the (+X) direction. The distance of the movement in the (+X) direction is equal to the half of the mutual arrangement pitch of the optical heads H0 to H7. After this movement is completed, the motor 18 is reversely rotated. Accordingly, the printed circuit board 20 moves in the (−Y) direction, while the optical heads H0 to H7 read the remaining parts of the images of the wiring patterns 22 and the through-holes 25.

In this manner, both scans indicated by the solid arrows A1 and the the broken arrows A2 in FIG. 1A are carried out. Thus the image reading of the entire surface of the printed circuit board 20 can be accomplished. The images detected are given to the data processor 300, wherein predetermined criteria are used to determine whether the printed patterns 22 and the through-holes 25 are defective or not based upon predetermined criteria.

C. Details of Optical Heads

Figure 3:
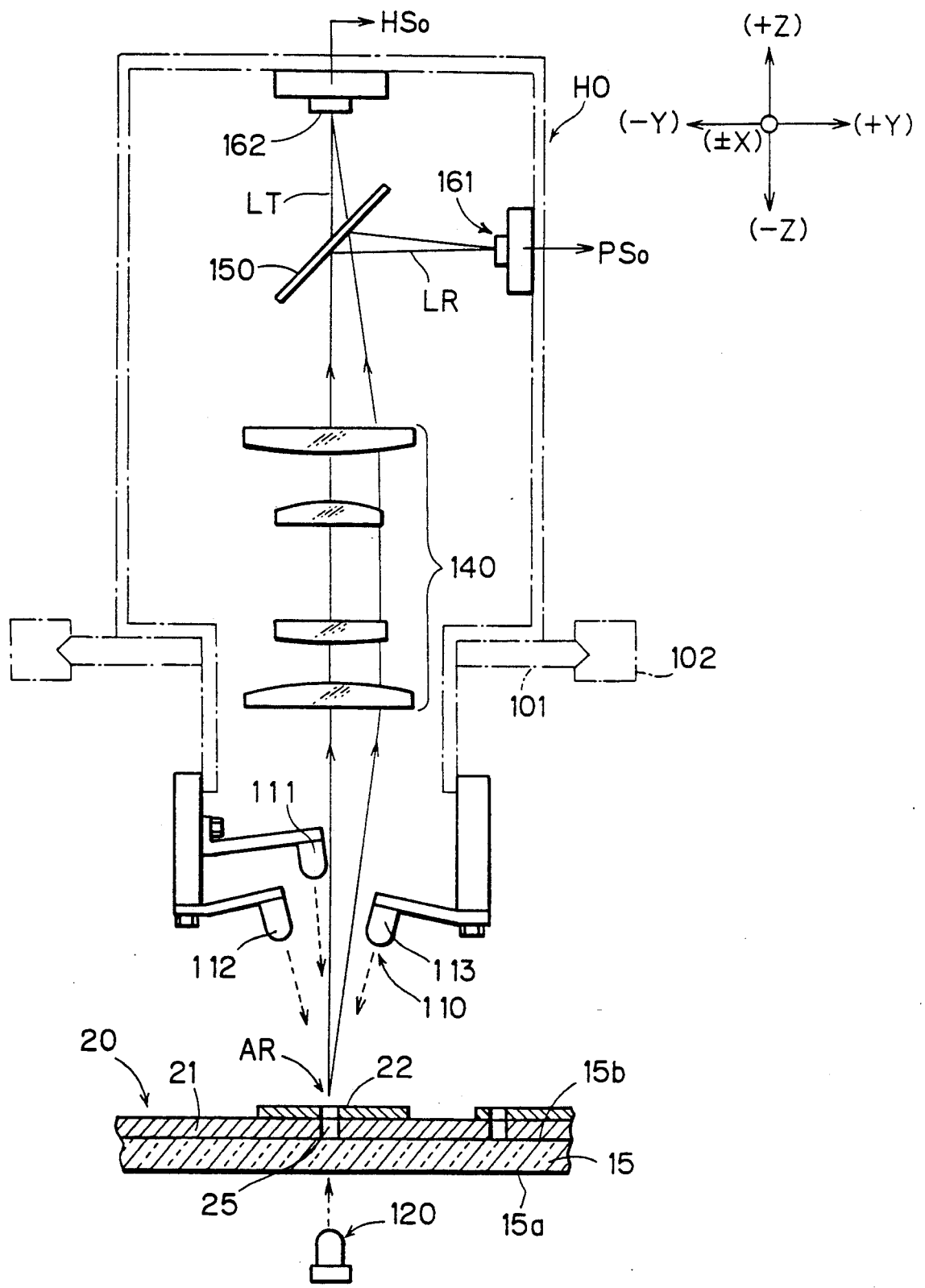
FIG. 3 is a typical side elevational view showing an optical head employed in the preferred embodiment.

FIG. 3 is a schematic side view of the internal structure of the optical head H0. Although FIG. 3 shows only the optical head H0, the other optical heads H1 to H7 have the same structure.

The light source 110 for reflected illumination is composed of a light source 111 for regular reflection and light sources 112 and 113 for irregular reflection. Each of the light sources 111, 112 and 113 is substantially a linear light source composed of a one-dimensional array of red LEDs which generate red light of wavelength $\lambda_1$ ($\fallingdotseq 600$ to 700 nm).

Light from the light sources 111, 112 and 113 is applied to the area-to-be-inspected or objective area AR of the top surface of the printed circuit board 20 located just under the optical head H0.

The light source 120 for transmitted illumination is composed of a one-dimensional array of infrared LEDs which generate infrared light of wavelength $\lambda_2$ ($\fallingdotseq 700$ to 1000 nm). The light source 120 projects the infrared light in the (+Z) direction toward an area corresponding to the reverse side of the area AR in the printed circuit board 20.

Part of the red light generated by the light sources 111, 112 and 113 for reflected illumination reaches the area AR and is reflected at the area AR. Part of the infrared light from the light source 120 for transmitted illumination reaches the through-holes 25 and passes through the through holes 25. The reflected light and the transmitted light thus obtained are directed to the optical head H0 as a spatially superposed compound light.

As shown in FIG. 3, the compound light passes through an image-formation lens system 140 and impinges on a cold mirror 150. The cold mirror 150 transmits only infrared rays. The red light (i.e., the reflected light LR from the surface of the printed circuit board 20) included in the compound light is reflected at the mirror 150 to the (+Y) direction so that an image is formed on a photo-detecting surface of a first CCD linear image sensor 161. The infrared light (i.e., the transmitted light LT through the through-hole 25) included in the compound light passes through the mirror 150 so that an image is formed on a photo-detecting surface of a second CCD linear image sensor 162.

Each of the CCD linear image sensors 161 and 162 has CCD photo-electric cells arranged one-dimensionally in the ($\pm X$) directions. The first linear image sensor 161 detects the one-dimensional image of the surface of the printed circuit board 20 illuminated by the reflected illumination. The second linear image sensor 162 detects the one-dimensional image of the through-hole 25 illuminated by the transmitted illumination. The movement mechanism shown in FIGS. 1A and 1B moves the printed circuit board 20 and the optical head array 100 in a manner so that each area of the printed circuit board 20 is scanned. As a result two-dimensional images of the wiring pattern 22 and the through-holes 25 for each area can be obtained.

D. Electric Structure and Operation

D-1. Overall Structure

Figure 4:
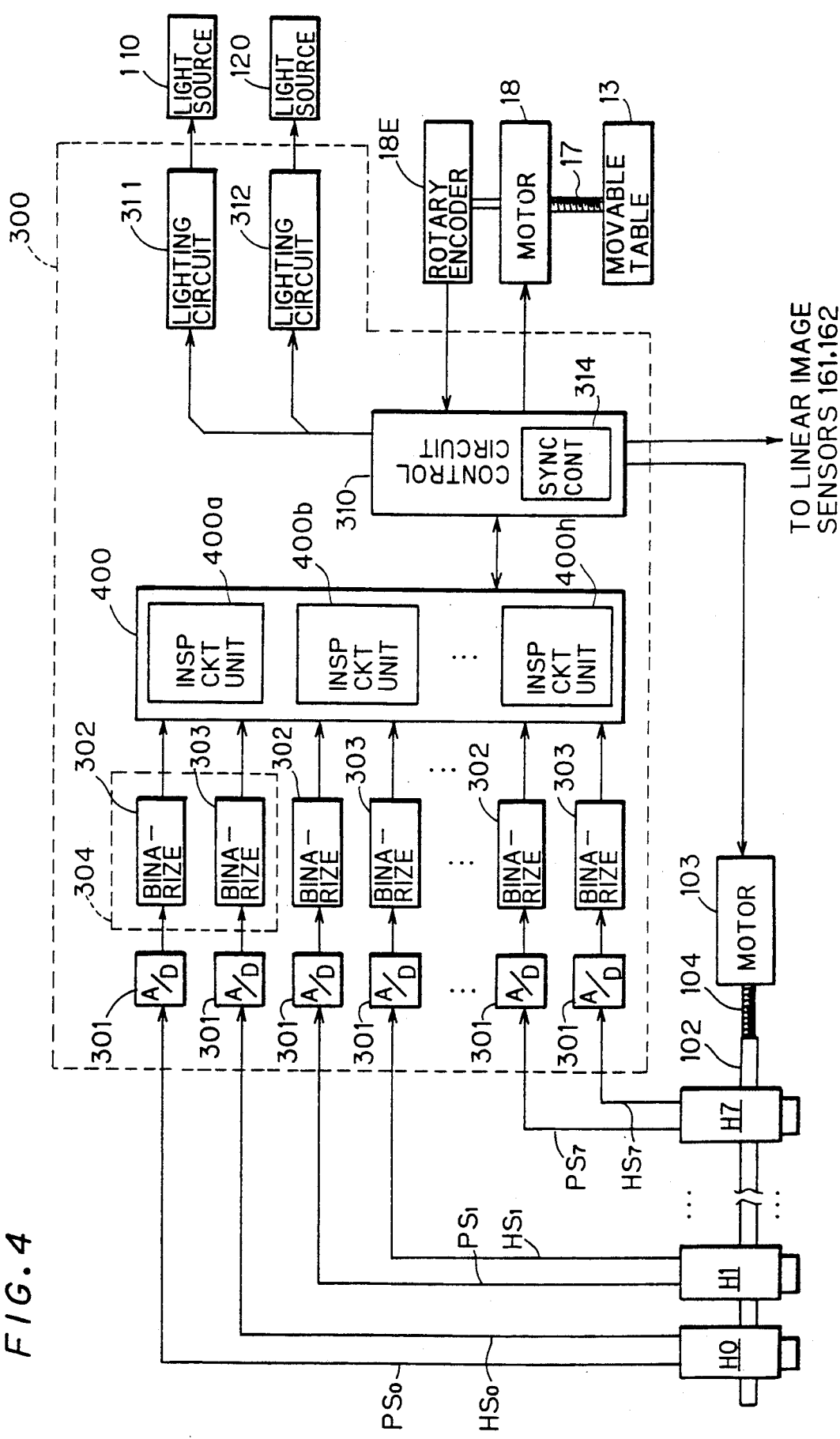
FIG. 4 is a block diagram showing the overall electrical structure of the preferred embodiment.

FIG. 4 is a block diagram of the overall electric structure of the preferred embodiment. A/D converters 301 receive wiring pattern image signals $PS_0$–$PS_7$ and through hole image signals $HS_0$–$HS_7$ from the optical heads H0 to H7 and convert them into digital signals. The digital signals are transmitted to circuits 304 each composed of binarizing circuits 302 and 303.

The binarizing circuits 302 and 803 compare the digitized image signals $PS_0$ and $HS_0$ with predetermined threshold values TH1 and TH2 (see FIG. 5) and output the respective binarized signals. The binarized signals are at a logical "H" level when the levels of the signals $PS_0$ and $HS_0$ are higher than the threshold values TH1 and TH2 respectively, and are at a logical "L" level when the levels of the signals $PS_0$ and $HS_0$ are lower than the threshold values TH1 and TH2, respectively. The binarizing circuits 302 and 308 corresponding to the other optical heads H1 to H7 have the same structure.

The binarized image signals thus obtained are transmitted to a pattern inspection system 400. The pattern inspection system 400 includes eight inspection circuit units 400a to 400h corresponding to the optical heads H0 to H7. The units 400a to 400h construct the two-dimensional images of the printed patterns 22 and the through-holes 25 based on the image signals which are supplied from the optical heads H0 to H7 and digitalized in the circuits 302 or 303. The units 400a to 400h operate to decide whether the printed patterns 22 and the through-holes 25 are defective or not based on predetermined criteria.

The data processor 300 further comprises a control circuit 310. The control circuit 310 provides on/off commands to the light sources 110 and 120 through lighting circuits 311 and 312, and drive control signals to the motors 18 and 103. The motor 18 is equipped with a rotary encoder 18E, which detects a motor rotation angle signal. The motor rotation angle signal for ruling data processing timing is given to the control circuit 310.

The control circuit 310 includes a synchronization control circuit 314 for controlling the read timing of the linear image sensors 161 and 162 and the synchronization of the motors 18 and 103.

D-2. Pre-processor

Figure 6A:
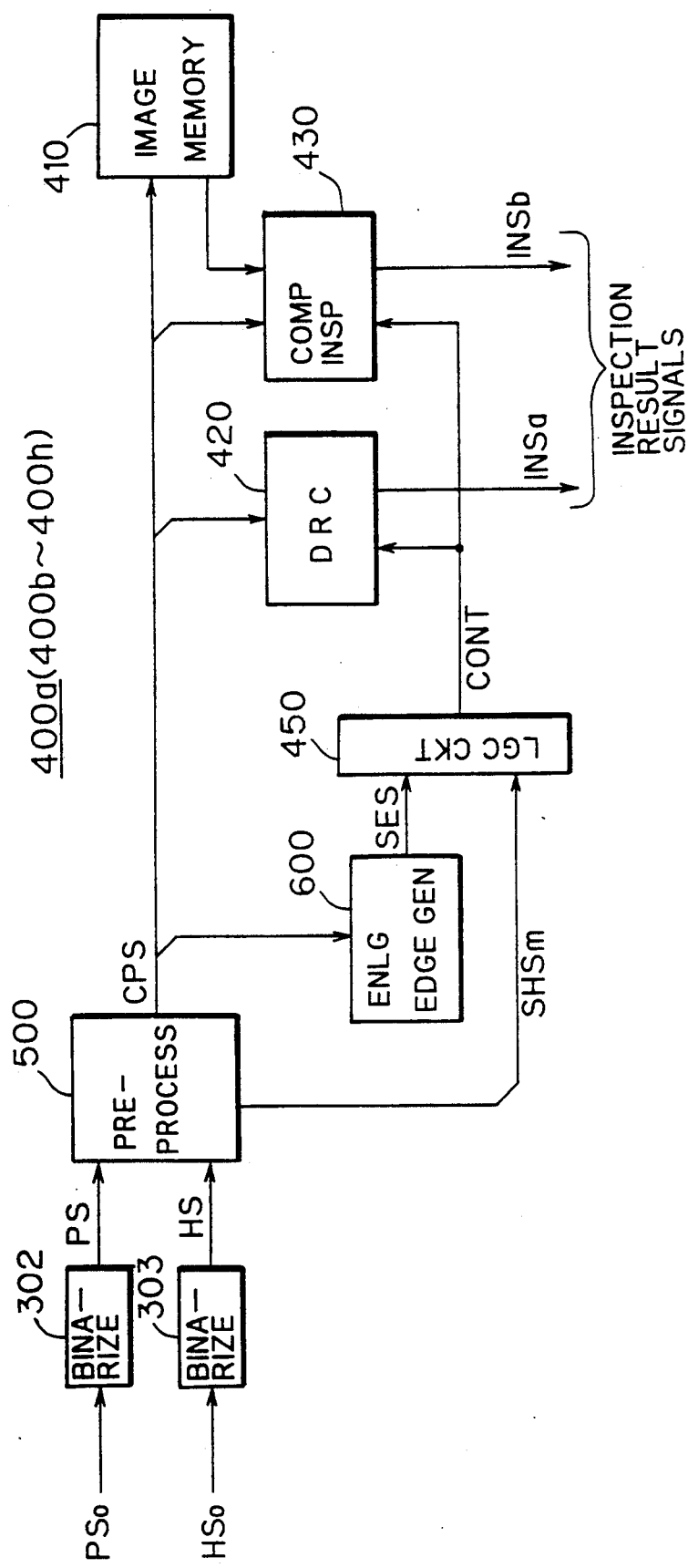
FIG. 6A is an internal structural diagram of an inspection circuit unit.

FIG. 6A is a block diagram of the internal structure of the inspection circuit unit 400a. The other inspection circuit units 400b to 400h have the same structure.

Figure 6B:
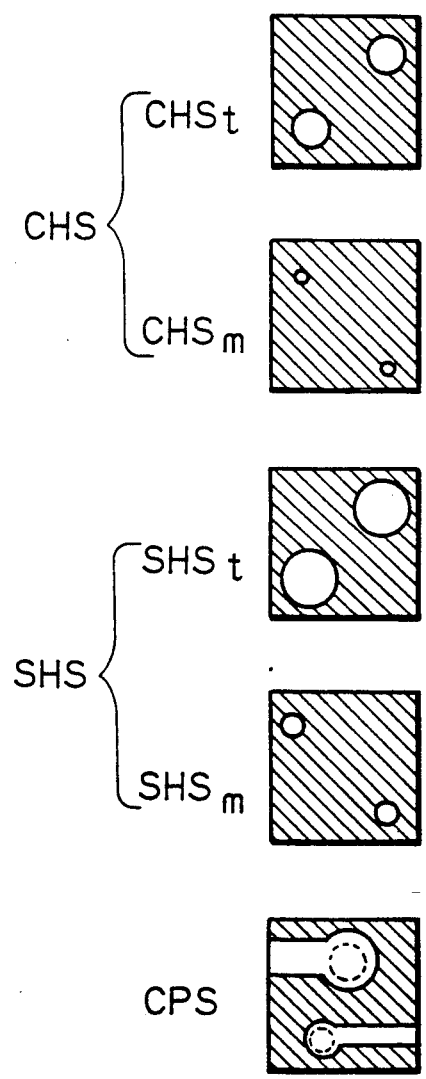
FIG. 6B is an explanatory diagram for signals produced in a pre-processing circuit.

The image signals PS and HS outputted from the binarizing circuits 302 and 303 are given to a pre-processor 500 as a pattern signal PS and a hole signal HS indicative of the two-dimensional images of the printed pattern 22 and the through-hole 25, respectively. The pre-processor 500 generates various signals based on the pattern signal PS and the hole signal HS. The major ones among the various signals are as follows (see FIG. 6B):

(1) Corrected hole signal CHS

This signal CHS represents a corrected hole image having a diameter obtained by slightly enlarging the diameter of the through-hole 25. The corrected hole signal CHS is generated in connection with detection of the inner wall of the through-hole 25. Namely, the inner wall of the through-holes 25 are plated with metal. However, the inner wall is sometimes detected neither in the pattern signal PS nor in the hole signal HS. Hence, the hole signal HS is enlarged or corrected to close or compensate for the gap caused between the signals PS and HS due to such an undetected portion. The corrected hole signal CHS includes a signal CHSt corresponding to the normal through-hole 25t and a signal CHSm corresponding to the mini-via-hole 25m.

(2) Enlarged hole signal SHS

This signal SHS represents an image obtained by further enlarging the hole diameter represented by the corrected hole signal CHS. The enlarged hole signal SHS includes an enlarged normal through-hole signal SHSt and an enlarged mini-via-hole signal SHSm.

(3) Compensated pattern signal CPS

Figure 5A:
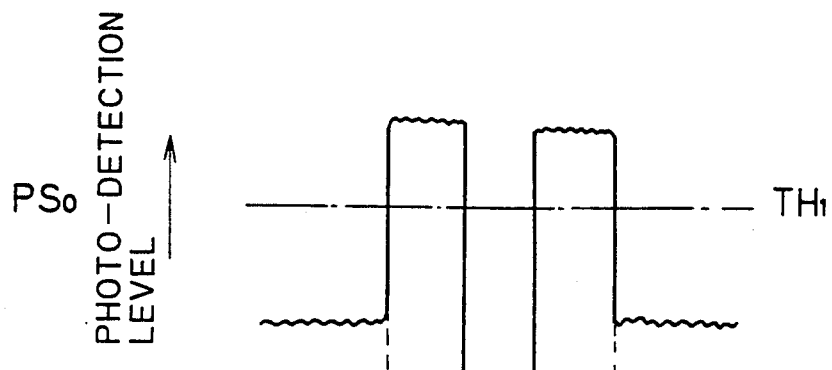
FIGS. 5(a) and 5(b) are explanatory diagrams for binarization of a print pattern and through holes.
Figure 5B:
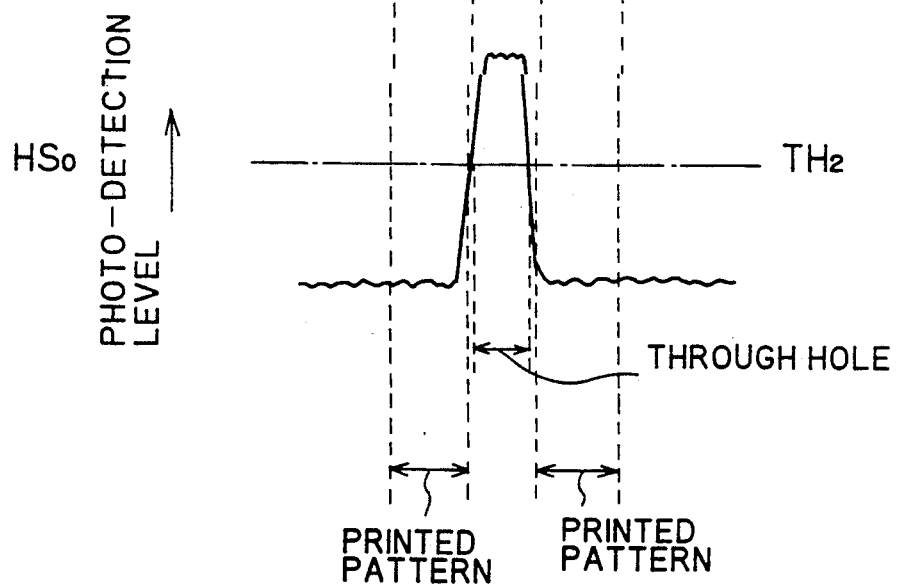
Figure 6C:
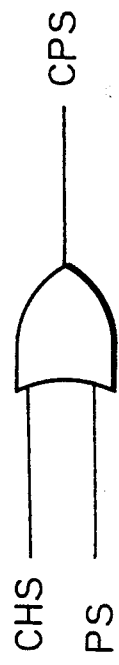
FIG. 6C illustrates an exemplary circuit structure for filling-up processing.

This is a signal in which a blank portion (or the center portion of FIG. 5(a)) corresponding to the through hole 25 in the pattern signal PS is filled in with a logical level "H". The signal CPS is the logical summation of the Corrected hole signal CHS and the pattern signal PS see FIG. 6C). The signal CPS is also referred to as a "corrected pattern signal" hereinafter.

These signals are used for various purposes. Shown in FIG. 6A are some of the signals outputted from the pre-processor 500 which are necessary for the following description.

D-3. Inspection Circuit

The inspection circuit unit 400a shown in FIG. 6A comprises the following two types of inspection circuits for pattern inspection:

(1) A DRC (design rule check) circuit 420

This circuit 420 is adapted to determine whether the printed board 20 is defective or nondefective by extracting characteristics such as line widths, pattern angles and continuity from the pattern on the printed board 20, and by determining whether or not these characteristics are out of the design values. Such DRC method or a characteristic extraction method is disclosed in Japanese Patent Laying-Open Gazette No. 57-149905 (1982).

(2) A comparative check circuit 430

This circuit 430 is adapted to compare image signals obtained from a previously prepared reference printed board with the image signals obtained from the printed board 20 to be inspected, and to specify the defective portions. The reference printed board is of the same type as the printed board 20 to be inspected and is previously determined as nondefective. This comparative method is disclosed in Japanese Patent Laying-Open Gazette No. 60-263807 (1985).

Since the device of the preferred embodiment requires information as to the reference printed board, the reference printed board is placed on the table 13 and its image is read before image reading is performed on the printed board 20 to be inspected. The signal CPS produced in the pre-processing circuit 500 in reading the reference printed board is supplied to and stored in an image memory 410. Address generation timing control for this image memory 410 and a region memory 630 (FIG. 6D), which is described later, is performed by the synchronization control circuit 314 shown in FIG. 4.

D-4. Extraction and Enlargement of Edge

Figure 6D:
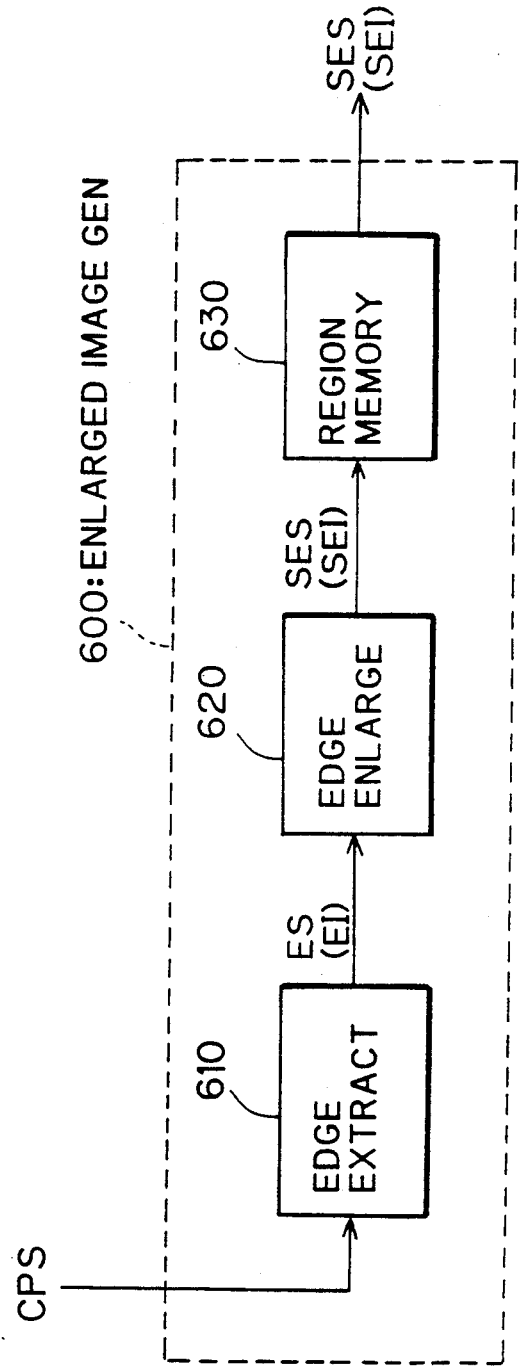
FIG. 6D is a block diagram showing the internal structure of an enlarged edge image generation circuit.

From the signals obtained in the pre-processing circuit 500 (FIG. 6A), the compensated pattern signal CPS is supplied also to an enlarged edge image generating circuit 600. As shown in FIG. 6D, the circuit 600 comprises an edge extraction circuit 610, an edge enlarging circuit 620 and the region memory 630.

Figure 7A:
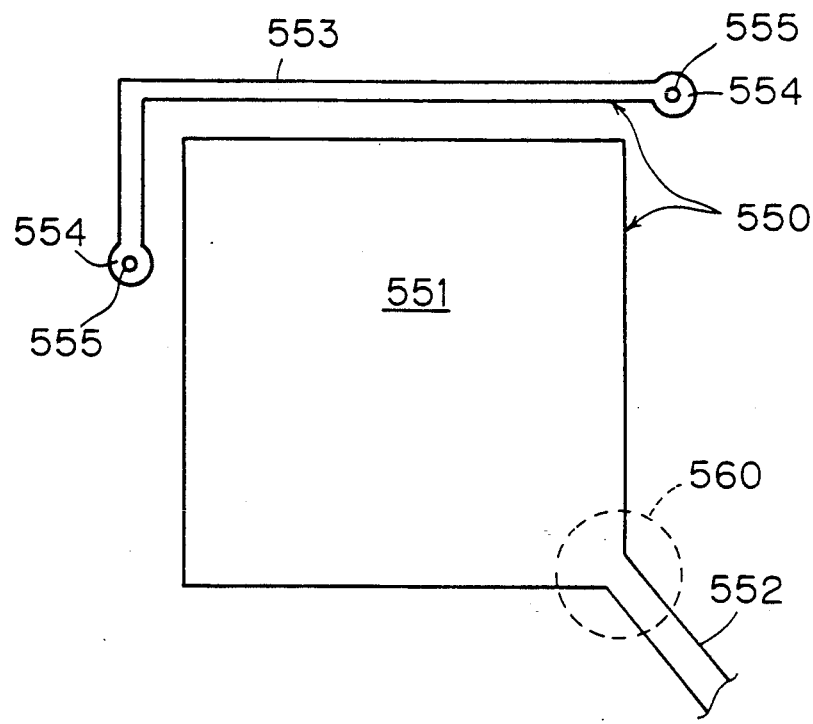
FIGS. 7A to 7C, 8A to 8C and 9A and 9B are explanatory diagrams for processes of generating enlarged edge images.
Figure 8A:
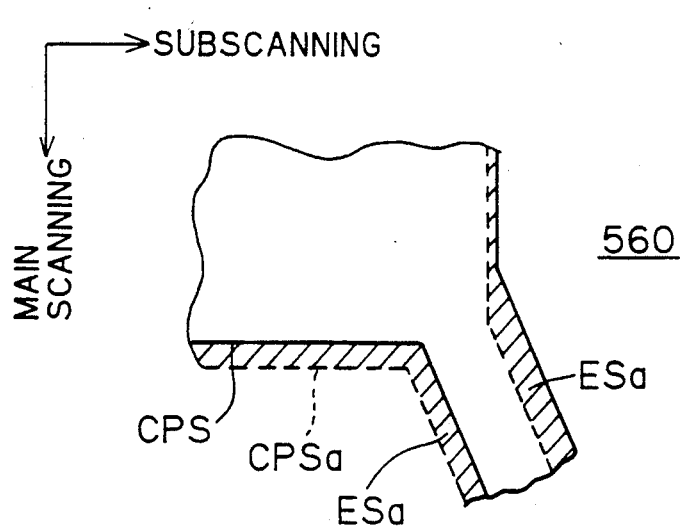

In connection with the operation of this circuit 600, FIG. 7A shows an exemplary print pattern on the reference printed board in the form of a partial plan view. This print pattern 550 has relatively narrow wiring patterns 552 and 553, in addition to a shielding portion or a copper solid portion 551. Through-holes 555 are formed in lands 554. The corrected pattern signal CPS obtained by reading such a pattern is supplied to a flip-flop circuit 611 (FIG. 10) provided in the edge extraction circuit 610, and is delayed in flip flop circuit 611 by a time period corresponding to one pixel, to become a signal $CPS_a$. The signals CPS an $CPS_a$ are then supplied to an exclusive OR (Ex. OR) gate 612. FIG. 8A is an enlarged view of portion 560 of FIG. 7A. Regions expressed in solid and broken lines in FIG. 8A correspond to the respective image regions represented by the signals CPS and $CPS_a$ which are supplied to the Ex. OR gate 612 at the same point in time. "MAIN SCANNING" and "SUBSCANNING" indicate image scanning operations in FIG. 1A along the ($\pm X$) direction and the ($\pm Y$) direction in FIG. 1A respectively, and whether the directions are of "+" or "−" depends on the pixel reading directions of the CCD linear image sensors 161 and 162 and the direction of movement of the table 13. Oblique line portions in FIG. 8A represent deviation areas between the images expressed by the signals CPS and $CPS_a$. An output signal $ES_a$ of the Ex. OR gate 612 expresses the deviation areas.

Figure 8B:
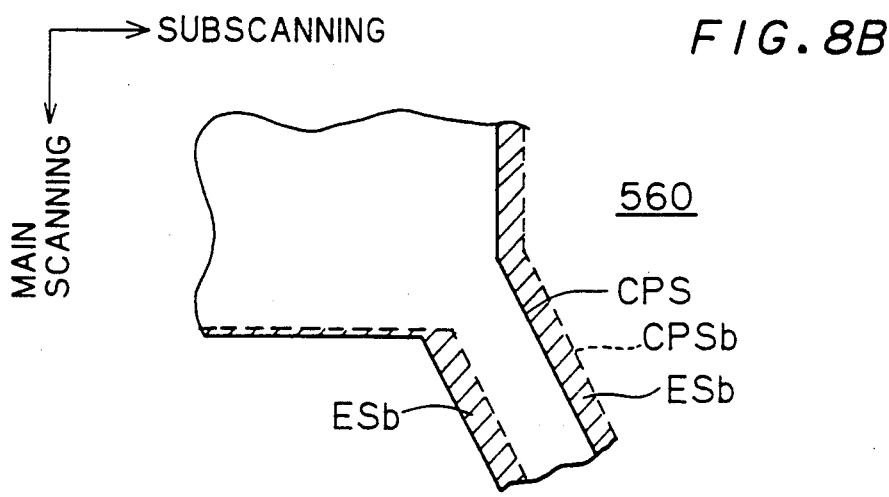
Figure 10:
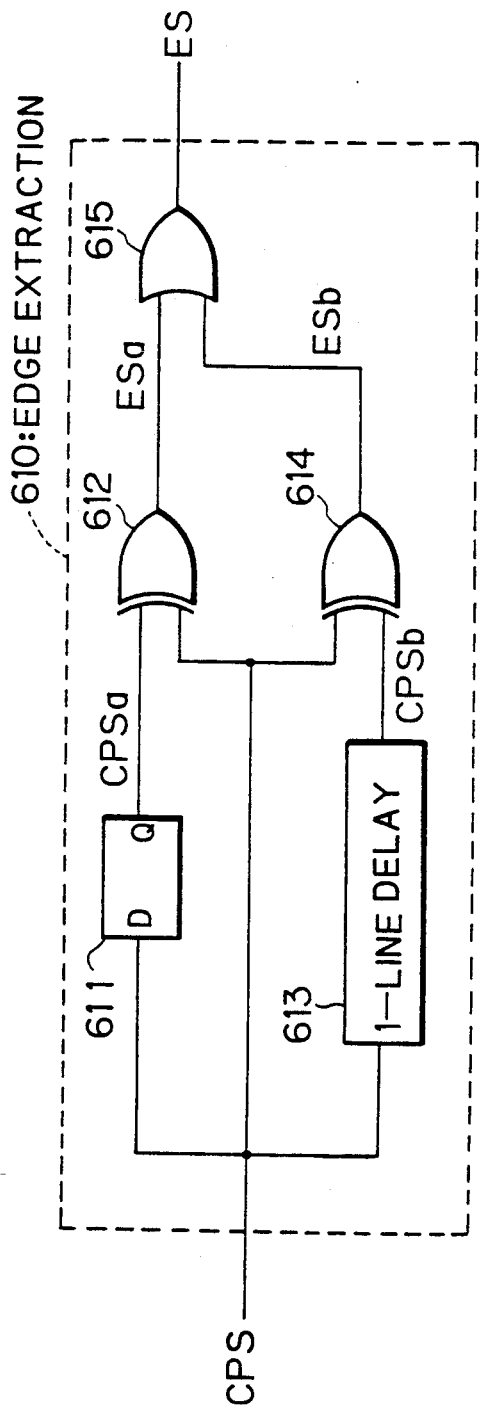
FIG. 10 is a circuit structure diagram showing an edge extraction circuit.

The corrected pattern signal CPS is also supplied to a one-scanning-line delay circuit 613 shown in FIG. 10, and delayed by this circuit 613 by a time period corresponding to one scanning line, to become a signal $CPS_b$. The signals CPS and $CPS_b$ are supplied to another Ex. OR gate 614. As shown in FIG. 8B, an output signal $ES_b$ from this Ex. OR gate 614 expresses deviation areas between the signals CPS and $CPS_b$ which are inputted in the Ex. OR gate 614 at the current point in time.

Figure 7B:
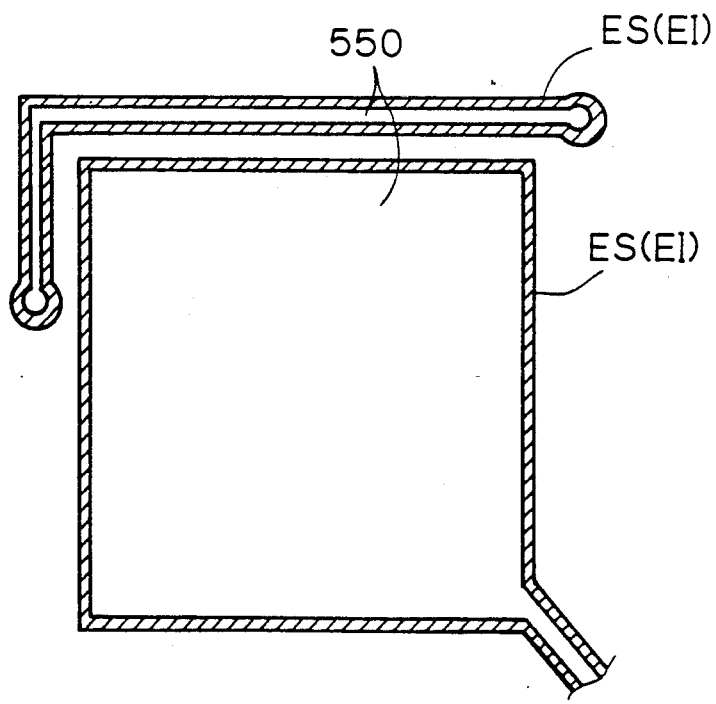
Figure 8C:
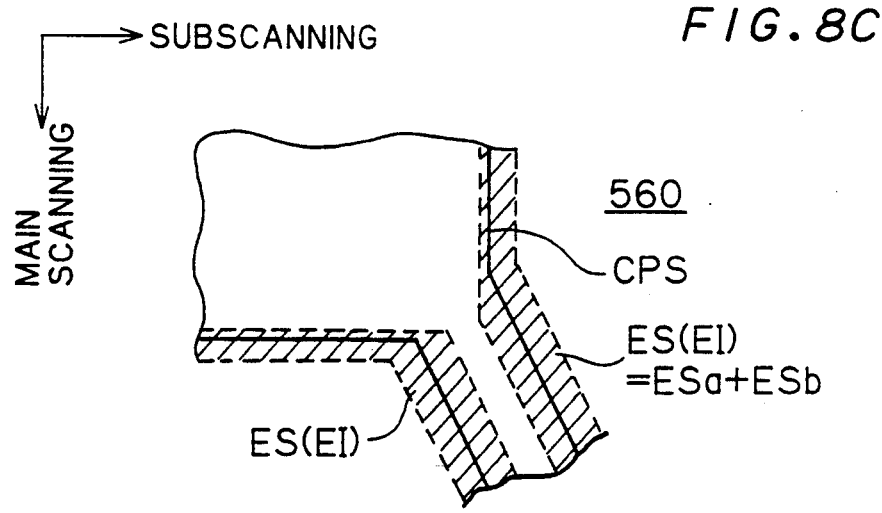

The respective output signals $ES_a$ and $ES_b$ of the two Ex. OR gates 612 and 614 are supplied to an OR gate 615, which in turn outputs a signal ES indicating the logical sum thereof. As shown in FIGS. 8C and 7B. the signal ES is an edge signal expressing each edge or contour line of the print pattern 550. An edge image EI expressed by this edge signal ES has a finite width. As shown in FIGS. 8A to 8C, the edge image IE may have a width of two or more pixels, by the combination of the signals $ES_a$ and $ES_b$, as to an edge obliquely extending with respect to each scanning direction, while the edge image EI has a width of one pixel in other edges.

Figure 9A:
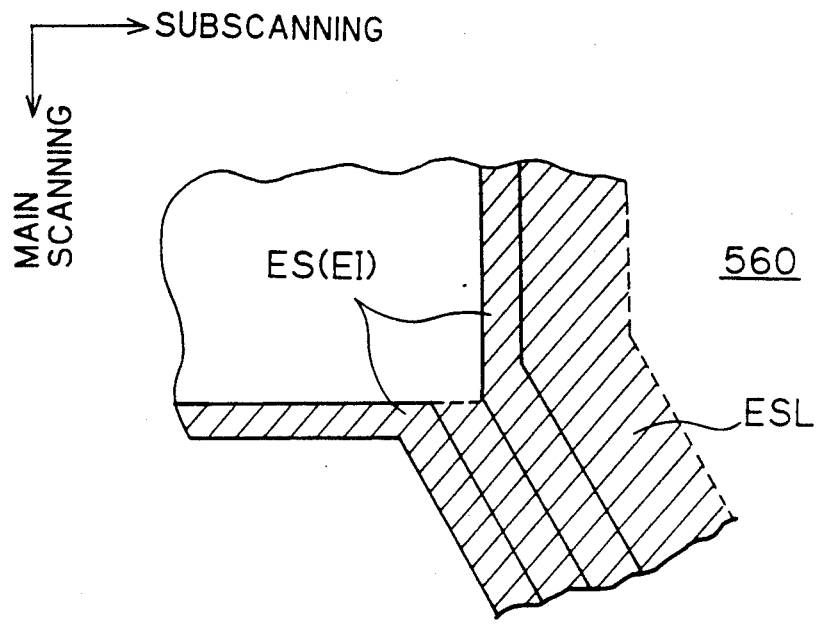
Figure 11:
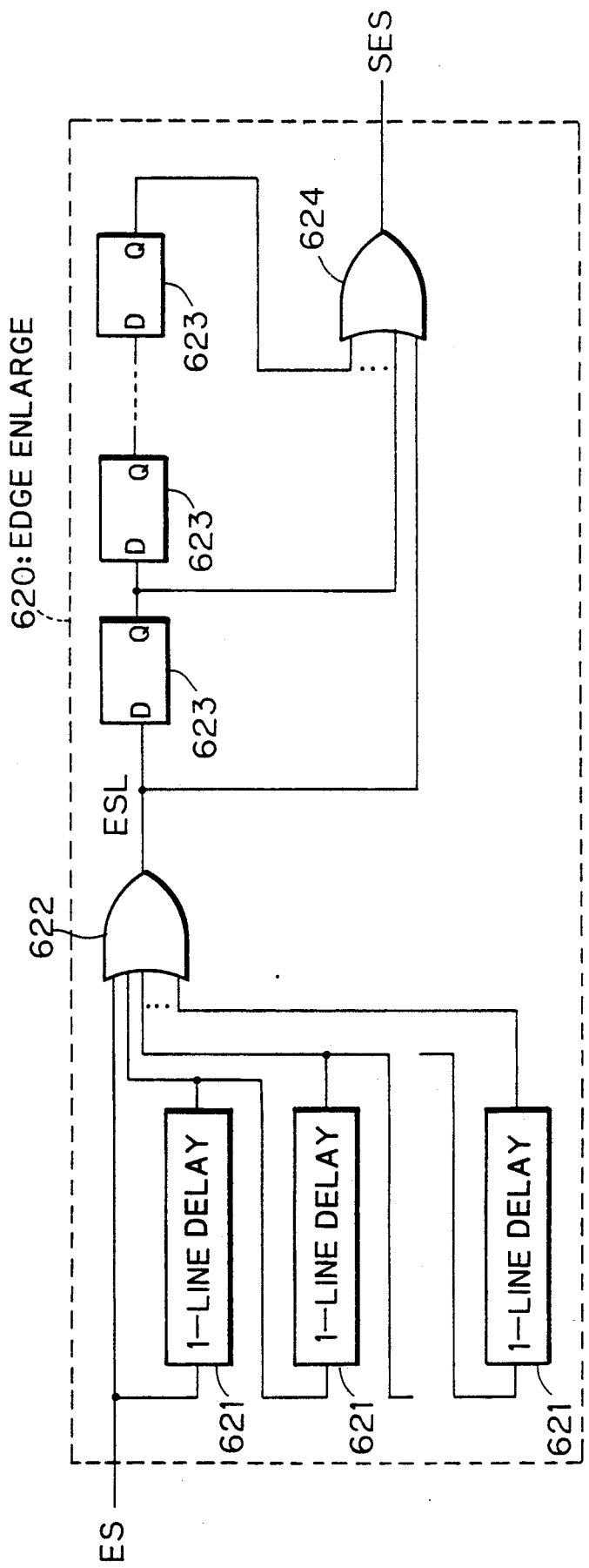
FIG. 11 is a circuit structure diagram showing an edge enlarging circuit.

The edge signal ES thus obtained is supplied to a multistage connection of one-line delay circuits 621 which are provided in the edge enlarging circuit 620 (FIG. 11). Assuming that represents a prescribed positive integer, the number of the one-line delay circuits 621 is (2n−1). Respective delay outputs of these (2n−1) one-line delay circuits 621 and the edge signal ES are supplied to an OR gate 622, which obtains a logical sum signal ESL thereof. As shown in FIG. 9A, this logical sum signal ESL expresses an image obtained by enlarging the edge image EI by 2n pixels in the subscanning direction.

Figure 7C:
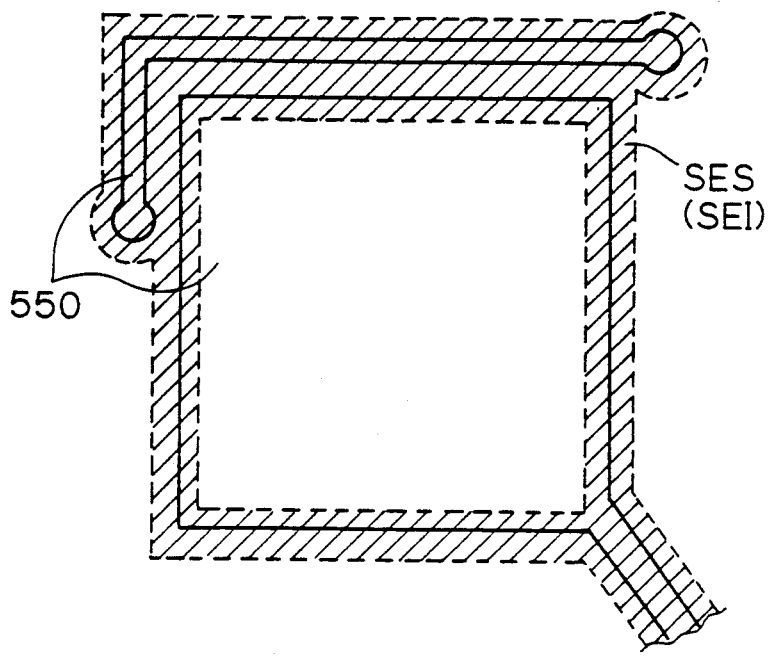
Figure 16:
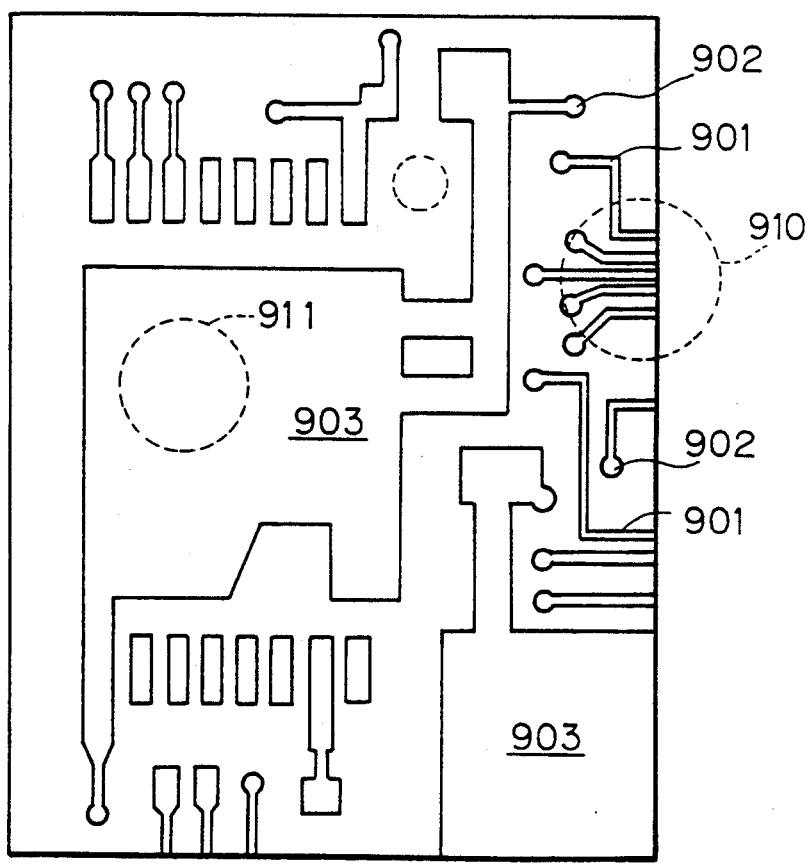
FIG. 16 is a diagram for illustrating a pattern on a printed board.
Figure 9B:
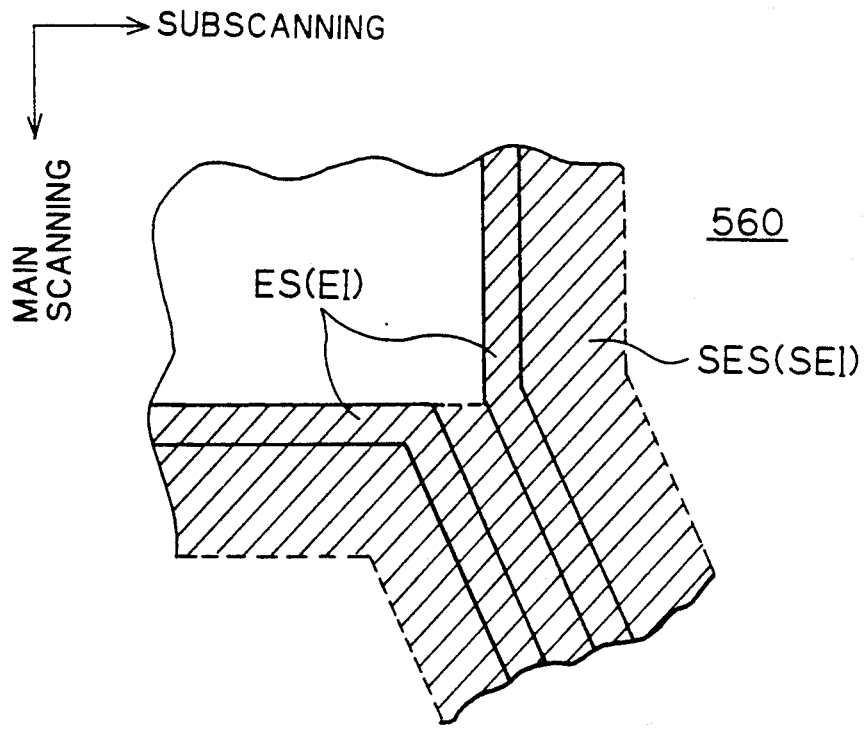

This signal ESL is supplied to (2n−1) multistage connections of flip-flop circuits 623, where each circuit 623 has a delay function of one pixel. Respective outputs of these flip-flop circuits 623 and the signal ESL are supplied to an OR gate 624. As shown in FIG. 9B, an output signal SES of the OR gate 624 expresses an image SEI which is obtained by enlarging the edge image EI by 2n pixels in both the main scanning direction and the subscanning direction respectively. The enlarged edge signal SES is supplied to the region memory 630 (FIG. 6D), so that the enlarged edge image SEI expressed by this signal SES is stored in this region memory 630. The center of the line width of the enlarged edge image SEI is deviated from the center of the edge image EI by n pixels in both the main scanning direction and the subscanning direction. However, it is possible to compensate for this deviation by delaying read timing by n pixels in the reading of the enlarged edge image SEI from the image memory 630. FIG. 7C shows the entire enlarged edge image SES as to the print pattern 550 shown in FIG. 7A.

D-5. Inspecting Operation

After the aforementioned processing of the reference printed board is completed, the reference printed board provided on the table 13 is replaced by the printed board 20 to be inspected, and image reading is started as to the board 20. The signal CPS outputted from the preparation circuit 500 of FIG. 6A is supplied to the DRC inspection circuit 420 and the comparative check circuit 430. In synchronization with this operation, the corrected pattern signal CPS as to the reference printed board, which had been stored in the image memory 410, is read and supplied to the comparative check circuit 430.

The DRC inspection circuit 420 and the comparative check circuit 430 execute respective inspection processing on the basis of respective input signals and output inspection result signals $INS_a$ and $INS_b$.

On the other hand, the enlarged mini-via-hole signal $SHS_m$ from the pre-processing circuit 500 is supplied to a logical composite circuit 450. In synchronization with this operation, the enlarged edge signals SES are read from the region memory 630 (FIG. 6D) sequentially along the scanning lines, and supplied to the logical composite circuit 450. The logical composite circuit 450 obtains the logical sum of the enlarged mini-via-hole signal $SHS_m$ and the enlarged edge signals SES, thereby generating an inspection control signal CONT. The inspection control signal CONT goes "H" in areas (hereinafter referred to as "important inspection areas") on the enlarged edge images SEI having no mini-via-holes 25m while going "L" in other areas. This inspection control signal CONT is supplied to inspection circuits 420 and 430, thereby selecting one inspection mode for the important inspection areas and selecting another inspection mode for other areas. Such elimination of the mini-via-holes 25m from the important inspection areas is related to the fact that no electronic components are mounted in the mini-via-holes 25m. The mini-via-holes 25m are provided in order to electrically connect the upper side and the lower side of the board 20 with each other using the plating layers formed on the inner wall portions thereof. Thus hole breakout is allowed to some extent so long as the connection is maintained. Therefore, the mini-via-holes 25m may be eliminated from the important inspection areas.

FIGS. 12A to 12D show exemplary structures for the selection of the respective inspection modes described above. FIGS. 12A to 12D represent inspection circuits 420 and 430. The contents of "processors" and "input image signals" in FIGS. 12A to 12D are different for the inspection circuits 420 and 430. Further, FIGS. 12A to 12D show hardware type "processors"; however, it is also possible to implement substantially equivalent functions thereto with software programs. The control signal CONT is used as an enabling signal for processor 421 in the example shown in FIG. 12A, so that the processor 421 is enabled only for the important inspection areas. Therefore, the device enters an inspection inhibiting mode in areas other than the important inspection areas. As a result, signal levels indicating "no defects" are given to inspection result signals $INS_a$ ($INS_b$) in the areas other than the important inspection areas.

Figure 12A:
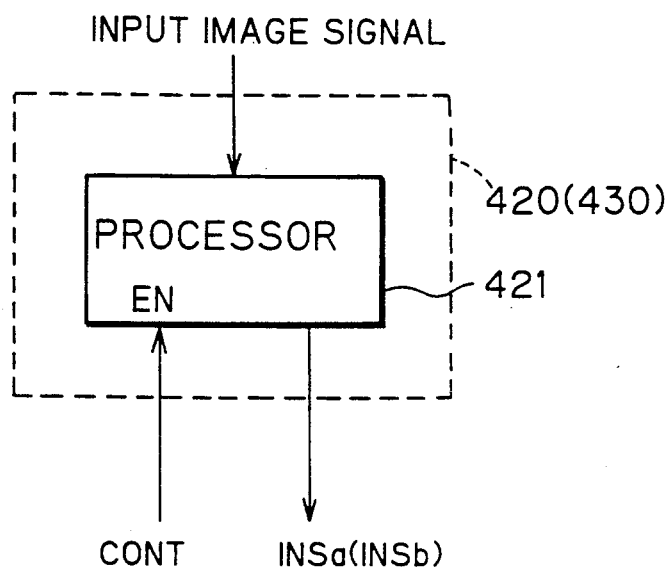
FIGS. 12A to 12D illustrate exemplary structures for selecting an inspection mode by a control signal.
Figure 12B:
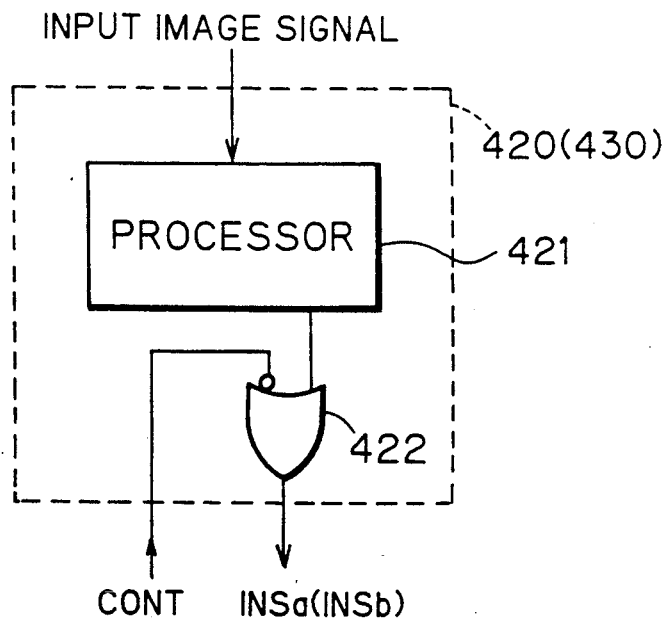

FIG. 12B shows that the selection of an inspection executing mode or the inspection inhibiting mode depending on the type of area, is performed using an OR gate 422. The result of the inspection meaning "no defects" is indicated when inspection result signals $INS_a$ ($INS_b$) are at a logical "H" level. The control signal CONT is at a logical "H" level for important inspection areas, while the same is at a logical "L" level for areas other than the important inspection areas.

Figure 12C:
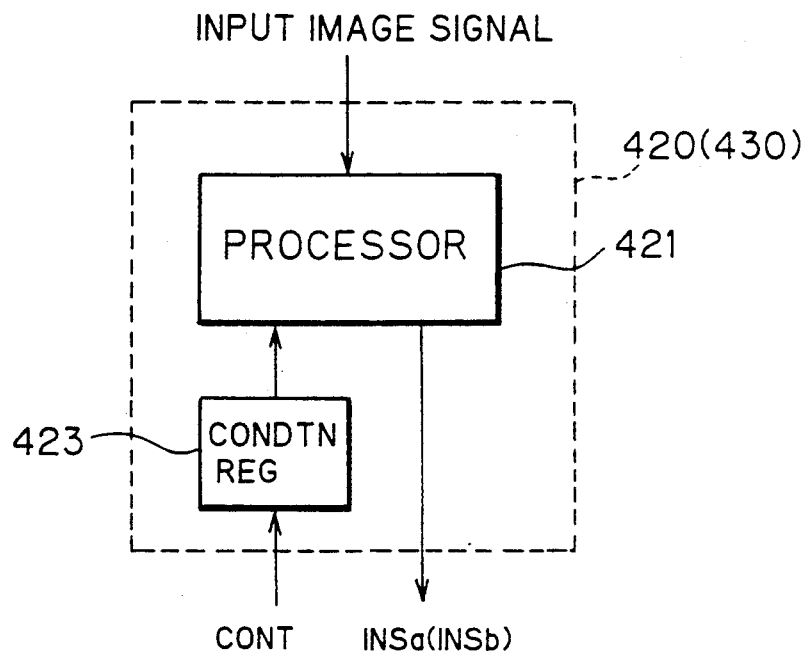

In the structure shown in FIG. 12C, a plurality of inspecting condition data defining different inspecting conditions is previously registered in a condition register 23. The different inspecting conditions include a relatively strict inspecting condition and a relatively loose inspecting condition. The relatively strict inspecting condition is a criterion such that printed boards having even small defects are regarded as defective ones, while the relatively loose inspecting condition is such that printed boards having only large defects are regarded as defective ones. In the important inspection areas, the data representing the relatively strict inspecting condition is read from the register 423 in response to the control signal CONT, and supplied to the processor 421. In areas other than the important inspection areas, on the other hand, the data representing the loose inspection condition is read from the register 423 and supplied to the processor 421. The processor 421 performs pattern inspections under an inspection mode defined by the inspecting condition thus supplied. Through this operation, a plurality of inspection modes defined by the respective inspection conditions are selectively employed for each area to be inspected.

Figure 12D:
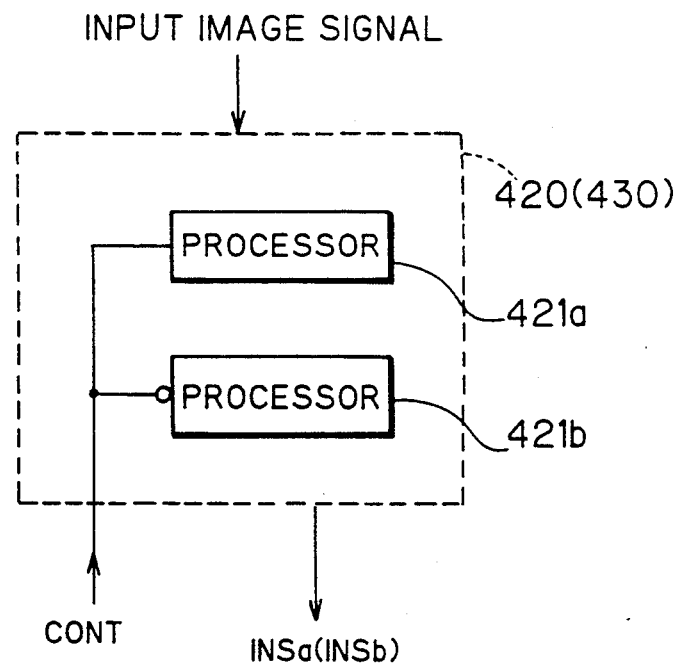

In the example shown in FIG. 12D, the are provided a plurality of processors 421a and 421b operable to conduct inspections corresponding to different inspection items. The processors 421a and 421b are selectively enabled depending on the level of the inspection signal CONT. Thereafter, an inspection item is selected depending on whether the area to be inspected belong to the important inspection area or not.

As described above in the various examples, one inspection mode is selectively employed for the important inspection areas and another for the other areas according to the preferred embodiment. Thus, it is possible to selectively inspect in detail peripheral areas of pattern edges, which are important in quality control. Hence, defects having low degrees of importance, such as pinholes in central regions of shielding patterns of a print pattern, are automatically neglected. As a result of this aspect of the present invention, it is possible to omit or simplify a later operation for confirming the defects, whereby the overall inspection process is improved.

Other Embodiments (1) The enlarged edge images SEI can also be obtained from a pattern image of the printed board 20 to be inspected. While the print pattern 22 on the printed board 20 may have defects, regions or areas requiring detailed inspection can be covered with the enlarged edge images so far as the edge enlarge width $2n$ is set at a relatively large value. Preferably, the edge enlarge width $2n$ is set at about 1 to 2 mm in real size on the printed board 20.

In the device of this preferred embodiment having a transmitted light source, it is also possible to read the pattern on a mask film employed for forming the printed board 20 and to obtain enlarged edge images SEI on the basis of the pattern image.

Figure 13:
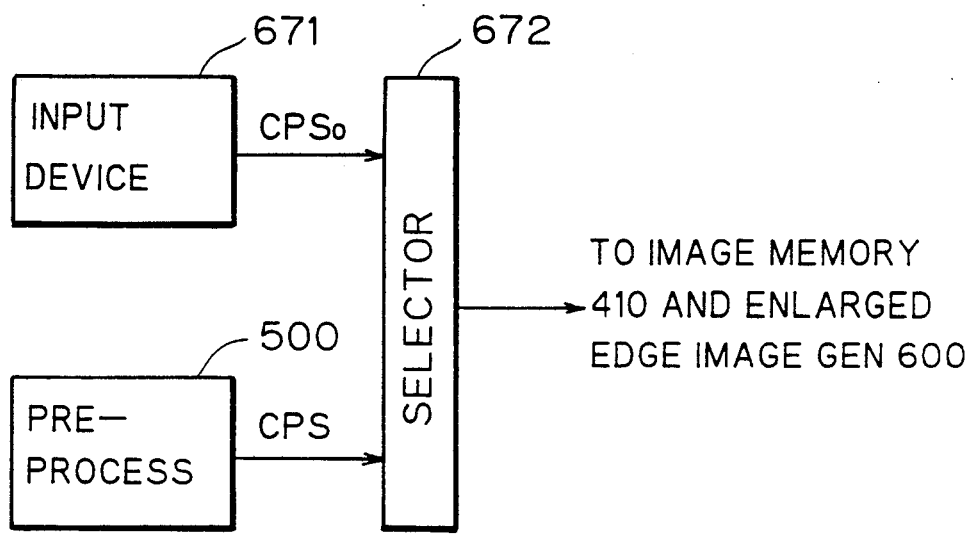
FIG. 13 is a partial diagram showing another preferred embodiment of the present invention.

(2) When the pattern on the printed board 20 is designed with a CAD, it is also possible to obtain enlarged edge images SEI using the CAD data. In this case, the CAD data is inputted using an input unit 671, as shown in FIG. 13. A selector 672 is adapted to switch the input thereof between respective output signals $CPS_0$ and CPS of the input unit 671 and a pre-processing circuit 500, and output the selected signal to an image memory 410, an enlarged edge image producing circuit 600 and the like. Before the image of the printed board 20 to be inspected is read, a filled-up pattern image signal $CPS_0$ produced from the CAD data is supplied to the image memory 410 and the enlarged edge image generating circuit 600. The enlarged edge image generating circuit 600 generates an enlarged edge signal SEI on the basis of this signal $CPS_0$, thereby defining important inspection areas.

Figure 14:
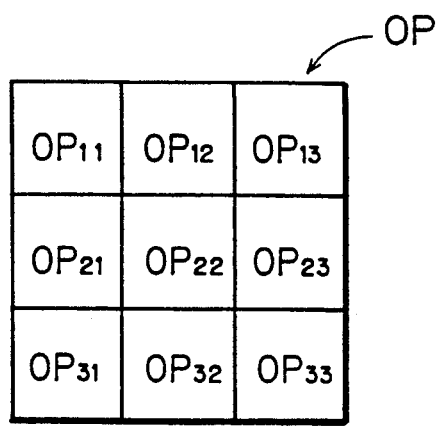
FIG. 14 is an explanatory diagram of a 3×3 space operator.

(3) The edge extraction circuit 610 can also be structured using a space operator. For example, a $3 \times 3$ space operator OP shown in FIG. 14 is made to act on respective pixels while sequentially matching its center $OP_{22}$ with the respective centers of pixels on the printed board. When a logical level which is different from the logical level at the central operator $OP_{22}$ is obtained in at least one of other operators $OP_{11}$ to $OP_{21}$ and $OP_{23}$ to $OP_{33}$ as a result of applying the space operator to respective pixels, the pixel of the central operator $OP_{22}$ is recognized as one of edge pixels.

Figure 15A:
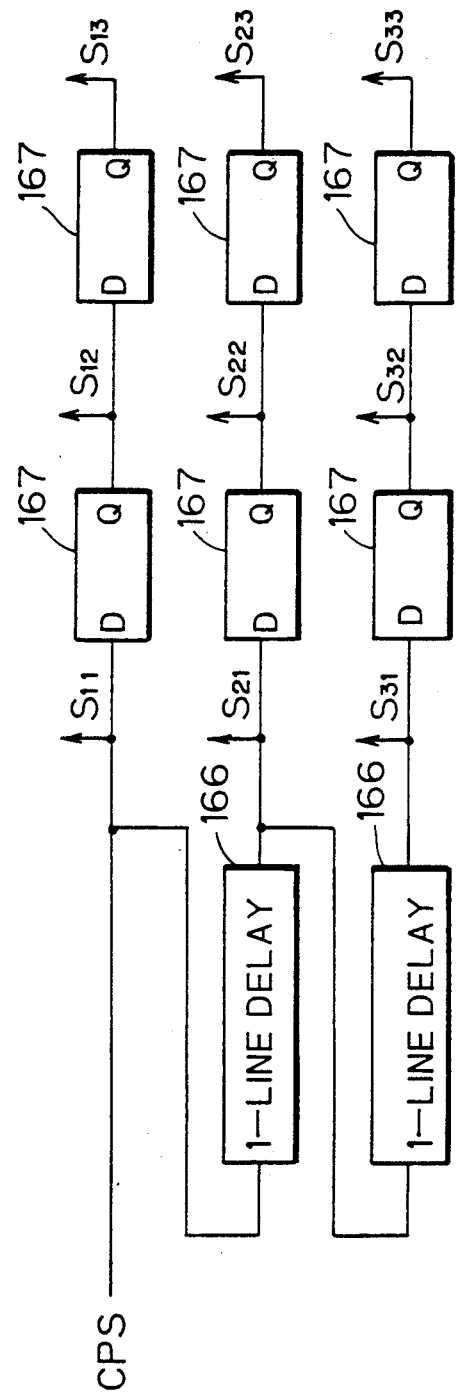
FIGS. 15A and 15B illustrate circuits corresponding to the 3×3 space operator shown in FIG. 14.
Figure 15B:
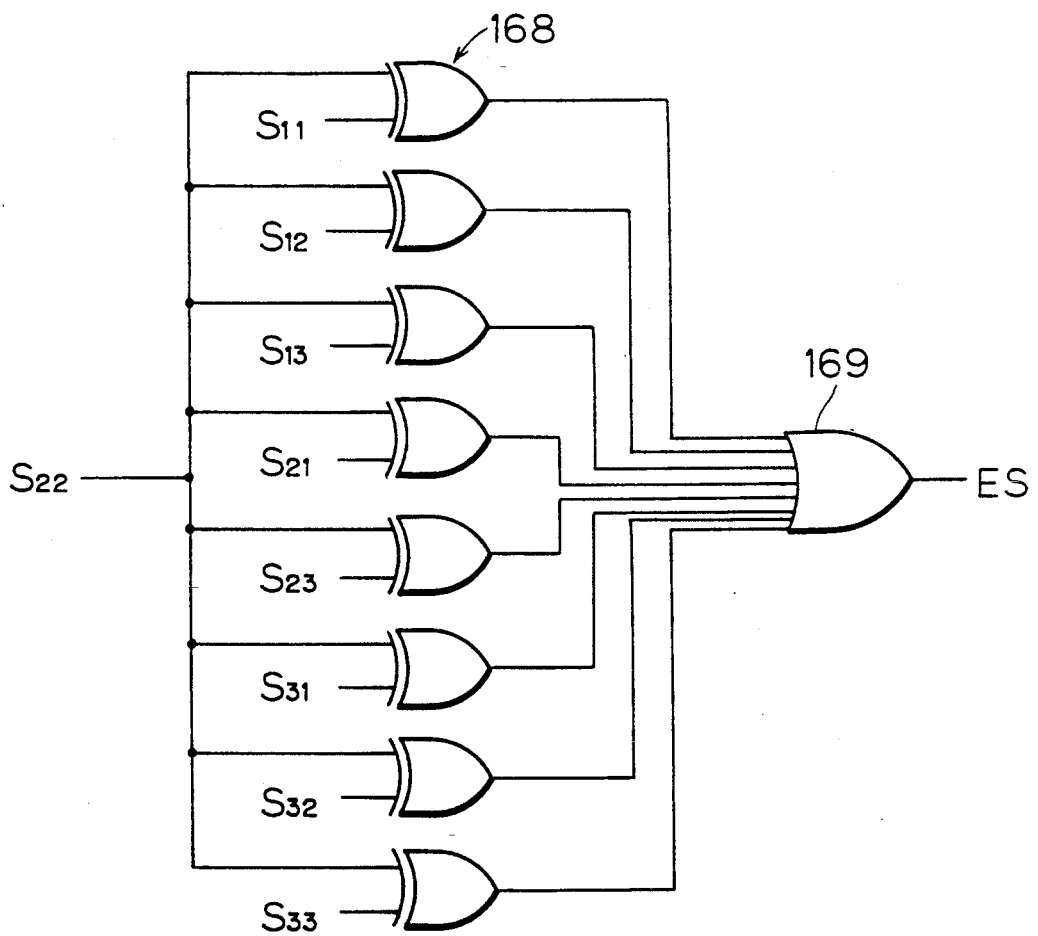

More particularly, signals $S_{11}$ to $S_{33}$ are produced by combination of one-line delay circuits 166 and flip-flop circuits 167 as shown in FIG. 15A. Then, the signals $S_{11}$ to $S_{33}$ are inputted in a combined circuit of an Ex. OR gate 168 and an OR gate 169 shown in FIG. 15B, to obtain the output Signal ES of the OR gate 169 as an edge signal.

(4) The enlarged edge images SEI may be produced on the basis of the pattern image signal PS whose blank part is not yet filled up. Further, two image reading systems may be provided so that the respective images of the printed board 20 to be inspected and the reference printed board can be simultaneously read.

The DRC inspection circuit 420 has the advantage that defect contents can be specified, while the comparative check circuit 430 has the advantage that a printed board having an arbitrary pattern can be inspected. Therefore, it is preferable to use both these inspection circuits as in the aforementioned preferred embodiment. However the present invention is applicable irrespective of the types of inspection circuits employed.

While the invention has been shown and described in detail, the foregoing description is in all aspects illustrative and not restrictive. It is therefore understood that numerous modifications and variations can be devised without departing from the scope of the invention.

I claim:

1. A method of inspecting an objective printed board having a conductive pattern thereon, said method comprising the steps of:
   (a) obtaining an image of said objective printed board, wherein said image includes an image of said conductive pattern;
   (b) extracting an edge from said image of said conductive pattern of from an image substantially equivalent to said image of said conductive pattern, to generate an edge image;
   (c) enlarging width of respective portions of siad edge image to generate an edge image;

(d) determining first and second areas in said image of said objective printed board, wherein said first area coincides with said enlarged edge image and said second area is an area other than said first area; and (e) inspecting said first area in a first inspection mode and inspecting said second area in a second inspection mode different from said first inspection mode.

2. The method of claim 1, wherein said first conductive pattern is a first conductive pattern;
said edge is an edge of said first conductive pattern; and
step (b) comprises the steps of:
(i) receiving an image of a reference printed board which i of the same type as said objective printed board and having a second conductive pattern previously judged as nondefective; and
(ii) obtaining said edge of said first conductive pattern as a function of said image of said reference printed board, to generate said edge image.

3. The method of claim 1, wherein
a mask film is used to form said conductive pattern of said objective printed board; and
the step (b) comprises the step of:
obtaining said edge of said conductive pattern from data representing a mask pattern on said mask film.

4. The method of claim 1, wherein
said conductive pattern of said objective printed board is determined in accordance with pattern design data; and
the step (b) comprises the step of:
obtaining said edge of said conductive pattern from said pattern design data.

5. The method of claim 2, wherein:
the step (a) comprises the steps of:
(i) setting said reference printed board in an image reader;
(ii) photoelectrically reading said image of said reference printed board with said image reader;
(iii) replacing said reference printed board with said objective printed board in said image reader; and
(iv) photoelectrically reading said image of said objective printed board with said image reader.

6. The method of claim 2, wherein:
the step (c) comprises the step of:
storing said enlarged edge image in memory means; and
the step (d) comprises the step of:
reading said enlarged edge image from said memory means to generate a signal indicative of said first area, which signal is employed in step (e) to switch said first and second inspection modes.

7. The method of claim 6, wherein:
said objective printed board is provided with through-holes having opening in said first conductive pattern;
said through-holes are classified into first type through-holes having a first diameter and second type through-holes having a second diameter smaller than said first diameter; and
step (a) further comprises the step of:
obtaining first hole image representing said first through-holes and second hole images representing said second through-holes;
step (d) further comprises the step of:

obtaining a logical summation of said enlarged edge image and said images of said second hole images to thereby generate said signal.

8. The method of claim 7, wherein:
step (a) comprises the steps of:
(i) obtaining images of said first through-holes of said second through-holes; and
(ii) enlarging said images of said first and second through-holes to obtain said first and second hole images, respectively.

9. The method of claim 2, wherein:
step (b) comprises the steps of:
(i) shifting said image of said reference board in a first direction to obtain a first shifted image;
(ii) shifting said image of said reference board in a second direction to obtain a second shifted image; and
(iii) obtaining a logical summation of said first and second shifted images to generate said edge image.

10. The method of claim 9, wherein:
the step (c) comprises the steps of:
(i) enlarging said edge image in said first direction to obtain a first enlarged image; and
(ii) enlarging said first enlarged image in said second direction to obtain said enlarged edge image.

11. The method of claim 1, wherein:
said first inspection mode is such that said first area is inspected according to a predetermined inspection procedure; and
said second inspection mode is such that inspection of said second area is inhibited 12. The method of claim 1, wherein:
said first inspection mode is such that said first area is inspected in a relatively strict condition for determining that said objective printed board is defective; and
said second inspection mode is such that said second area is inspected in a relatively loose condition for determining that said objective printed board is defective.

13. The method of claim 1, wherein:
said first inspection mode is such that said first area is inspected for a first inspection item for determining that said objective printed board is defective; and
said second inspection mode is such that said second area is inspected for a second inspection item for determining that said objective printed board is defective.

14. A device of inspecting an objective printed board having a conductive pattern thereon, said device comprising:
(a) means for obtaining an image of said objective printed board, wherein said image includes an image of said conductive pattern;
(b) means for extracting an edge of said conductive pattern from said image of said conductive pattern or from an image substantially equivalent to said image of said conductive pattern, to generate an edge image;
(c) means for enlarging width of respective portions of said edge image to generate an enlarged edge image;
(d) means for determining first and second areas in said image of said objective printed board, wherein said first area coincides with said enlarged edge image and said second area is an area other than said first area; and (e) means for inspecting said first area in a first inspection mode and inspecting said second area in a second inspection mode different from said first inspection mode.

15. The device of claim 14, wherein
said conductive pattern of said objective printed board is a first conductive pattern;
said edge of said conductive pattern is an edge of said first conductive pattern; and
said means (b) comprises:
- (i) means for receiving an image of a reference printed board which is of the same type as said objective printed board and having a second conductive pattern previously judged as nondefective; and
- (ii) means for obtaining said edge of said first conductive pattern as a function of said image of said reference printed board, to generate said edge image.

16. The device of claim 14, wherein
a mask film is used to form said conductive pattern of said objective printed board; and
said means (b) comprises:
means for obtaining said edge of said conductive pattern from data representing a mask pattern on said mask film.

17. The device of claim 15, wherein
said conductive pattern of said objective printed board is determined in accordance with a pattern design data; and
said means (b) comprises:
means for obtaining said edge of said conductive pattern from said pattern design data.

18. The device of claim 15, wherein:
said objective printed board is provided with through-holes having openings in said first conductive pattern; and
said means (a) comprises:
- (i) a horizontal transparent plate capable of holding said objective printed board thereon in a state that a bottom surface of said objective printed board is in contact with said transparent plate;
- (ii) first light source means provided above said transparent plate for illuminating a top surface of said objective printed board;
- (iii) second light source means provided under said transparent plate for illuminating said bottom surface of said objective printed board through said transparent plate; and
- (iv) means for photoelectrically reading said image of said objective printed board illuminated by said first and second light source means;
wherein a first light emitted from said first light source means is reflected at said top surface and is received by said means (iv); and a second light emitted from said second light source means transmits through said through-holes and is received by said means (iv).

19. The device of claim 15, wherein:
said means (c) comprises:
memory means for storing said enlarged edge image; and
said means (d) comprises:
means for reading said enlarged edge image from said memory means to generate a signal indicative of said first area, which signal is employed in said means (e) to switch said first and second inspection modes.

20. The device of claim 19, wherein:
said objective printed board is provided with through-holes having openings in said first conductive pattern;
said through-holes are classified into first type through-holes having a first diameter and second type through-holes having a second diameter smaller than said first diameter; and
said means (a) further comprises:
means for obtaining first hole images representing said first through-holes and second hole images representing said second through-holes;
said means (d) further comprises:
means for obtaining logical summation of said enlarged edge image and said images of said second hole images to thereby generate said signal.

21. The device of claim 20, wherein:
said means (a) comprises:
- (i) means for obtaining images of said first through-holes and said second through-holes; and
- (ii) means for enlarging said images of said first and second through-holes to obtain said first and second hole images, respectively.

22. The device of claim 15, wherein:
said means (b) comprises:
- (i) means for shifting said image of said reference board in a first direction to obtain a first shifted image;
- (ii) means for shifting said image of said reference board in a second direction to obtain a second shifted image; and
- (iii) means for obtaining a logical summation of said first and second shifted images to generate said edge image.

23. The device of claim 22, wherein:
said means (c) comprises:
means for enlarging said edge image in said first direction to obtain a first enlarged image; and
means for enlarging said first enlarged image in said second direction to obtain said enlarged edge image.

24. The device of claim 14, wherein:
said first inspection mode is such that said first area is inspected according to a predetermined inspection procedure; and
said second inspection mode is such that inspection of said second area is inhibited.

25. The device of claim 15, wherein:
said first inspection mode is such that said first area is inspected in a relatively strict condition for determining that said objective printed board is defective; and
said second inspection mode is such that said second area is inspected in a relatively loose condition for determining that said objective printed board is defective.

26. The device of claim 15, wherein:
said first inspection mode is such that said first area is inspected for a first inspection item for determining that said objective printed board is defective; and
said second inspection mode is such that said second area is inspected for a second inspection item for determining that said objective printed board is defective.

* * * * *